United States Patent [19]

Yamakoshi et al.

[11] Patent Number: 4,597,393
[45] Date of Patent: Jul. 1, 1986

[54] ARTERIAL PRESSURE MEASURING APPARATUS

[75] Inventors: Ken-ichi Yamakoshi, Sapporo; Hideaki Shimazu, Tokyo, both of Japan

[73] Assignee: Kabushiki Kaisha Copal Takeda Medical Kenyusho, Tokyo, Japan

[21] Appl. No.: 594,353

[22] Filed: Mar. 28, 1984

[30] Foreign Application Priority Data

Mar. 31, 1983 [JP] Japan ............................ 58-56135

[51] Int. Cl.[4] ............................................. A61B 5/02
[52] U.S. Cl. .............................. 128/677; 128/667
[58] Field of Search ........................ 128/664–667, 128/672, 677, 680–683

[56] References Cited

U.S. PATENT DOCUMENTS

| | | | |
|---|---|---|---|
| 2,826,191 | 3/1958 | Burns | 128/682 |
| 3,585,987 | 6/1971 | Svensson | 128/672 |
| 4,030,485 | 6/1977 | Warner | 128/667 |
| 4,425,921 | 1/1984 | Fujisaki et al. | 128/664 X |
| 4,427,013 | 1/1984 | Nunn et al. | 128/681 |

FOREIGN PATENT DOCUMENTS 0876105 11/1981 U.S.S.R. ........................... 128/666

Primary Examiner—Kyle L. Howell
Assistant Examiner—Angela D. Sykes
Attorney, Agent, or Firm—McAulay, Fields, Fisher, Goldstein & Nissen

[57] ABSTRACT

An arterial pressure measuring apparatus which comprises in combination a cuff adapted to be applied to a portion a human body where arterial pressure is measured, a light emitting diode, a phototransistor, a transducer, a pump for the control of the cuff, a control unit for the pump, a transducer for measuring the pressure of the cuff, a current control circuit for the light emitting diode, a DC amplifier circuit, an AC amplifier circuit for the output of the phototransistor and an operation circuit.

20 Claims, 20 Drawing Figures

VARIATION IN VOLUME WITHIN BLOOD VESSEL mℓ

ARTERIAL PRESSURE MEASURING APPARATUS

BACKGROUND OF THE INVENTION

This invention relates to a non-visible arterial pressure measuring apparatus and more particularly, to an arterial pressure measuring apparatus which can accurately measure lowest arterial pressure.

The conventional indirect measurement of arterial pressure has been generally conducted by detecting Korotkov sound (K sound). However, since the origin and mechanism of K sound has not been perfectly made clear, the accuracy of the indirect measurement of arterial pressure has not been high even if the electronic measurement is utilized.

On the other hand, of late, it has been also known that an arterial pressure measuring apparatus utilizing the oscillation process in which an arterial pressure value is sought from the oscillation of blood at a very low pressure in a part of a human body where the arterial pressure measurement is to be made and compressed by the cuff. However, such an apparatus is in principle applicable to mean arterial pressure measurement, but the theoretical base on which diastolic pressure measurement is made possible is feeable.

SUMMARY OF THE INVENTION

The purpose of the present invention is to provide an arterial pressure measuring apparatus which accurately seeks diastolic pressure values from systolic and mean arterial pressure values measured by known means highest, lowest and mean values based on arterial pulse waves or volume pulse waves corresponding to one heart beat, respectively and arterial pressure constants and volume wave form constants.

The above and other objects and attendant advantages of the present invention will be more readily apparent to those skilled in the art from a reading of the following detailed description in conjunction with the accompanying drawings which show preferred embodiments of the invention for illustration purpose only, but not for limiting the scope of the invention.

PREFERRED EMBODIMENTS OF THE INVENTION

The present invention will be now described referring to the accompanying drawings.

Figure 1:
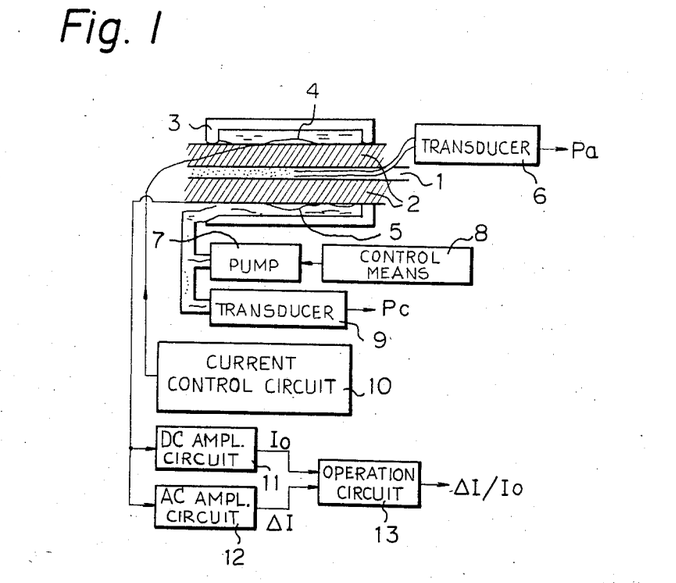
FIG. 1 is a schematic view of an experimental apparatus showing the principle of the present invention.

First of all, FIG. 1 is a schematic view of an experimental apparatus which is adapted to measure arterial pressure in human fingers for explanation of the principle of blood pressure measurement. In FIG. 1, 1 denotes an arteria, 2 denotes tissues, 3 does cuff, 4 denotes a light emitting diode as light emitting element, 5 denotes a phototransistor as light receiving element, 6 denotes a transducer for measuring arterial pressure directly, 7 denotes a pump for controlling the cuff 3, 8 denotes control means for the pump, 9 denotes a transducer for measuring pressure in the cuff, 10 denotes the current control circuit for the light emitting diode 4, 11 denotes the DC amplifier circuit of the output of the phototransistor 5, 12 denotes the AC amplifier circuit for the output of the phototransistor 5 and 13 denotes an operation circuit for calculating the ratio of the output of the DC amplifier circuit 11 to that of the AC amplifier circuit 12.

The experimental apparatus is adapted to directly detect by the use of an optical sensor the movement of arterial vessel walls in the central portion of a human finger under pressure by the cuff 3 and a volume oscillation apparatus for measuring systolic and mean arterial pressures based variation in the amplitude of photoelectric pulse waves as the pressure of the cuff 3. The light emitting diode 4 and phototransistor 5 are arranged facing each other in the measuring zone right below the cuff 3.

In the construction and arrangement of the experimental apparatus of the type mentioned just above, in operation, the light Ii emitted from the light emitting diode 4 is absorbed in different portions such as the arteria 1 system, the vein system and the tissues 2 and the amount of light passing through the different portions is detected by the phototransistor 5. When the Beer's law can be applied to the entire system, variation in volume ΔV in proportion to that of arterial pressure in the arterial pressure system 1 will be measured by the following equation:

$$\Delta V = k \cdot \ln[1 + (\Delta I/I.)] \quad (1)$$

wherein
- k: Constant determined by concentration and absorption coefficient of absorption of absorption material for arterial pressure,
- ΔI: Variation in quantity of light passing through the arterial vessel system following heart beat; and
- I.: Mean brightness of the light coming into the phototransistor.

In the system mentioned above, if ΔI is sufficiently smaller than I., the above-equation (1) can be approximated to the following:

$$\Delta V = k \cdot (\Delta I/I.) \quad (2)$$

Figure 2:
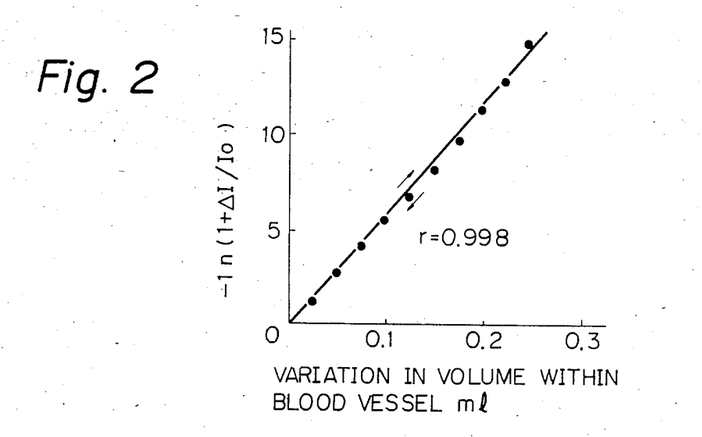
FIG. 2 is a diagram showing the relationship between variation in the volume of blood in a blood vessel measured by the direct method and variation in the volume of blood in a blood vessel measured by the indirect method according to the present invention.

The diagram of FIG. 2 confirms the pertinence of the system by the apparatus of FIG. 1 when the system is applied to a model blood vessel bed and as seen from this figure, it will be understood that ΔV can be detected with excellent rectilinearity. That is, the correlative coefficient r between the result detected directly by the transistor 6 and the result detected by the system employing the apparatus according to the present invention is: r=0.998.

Figure 3A:
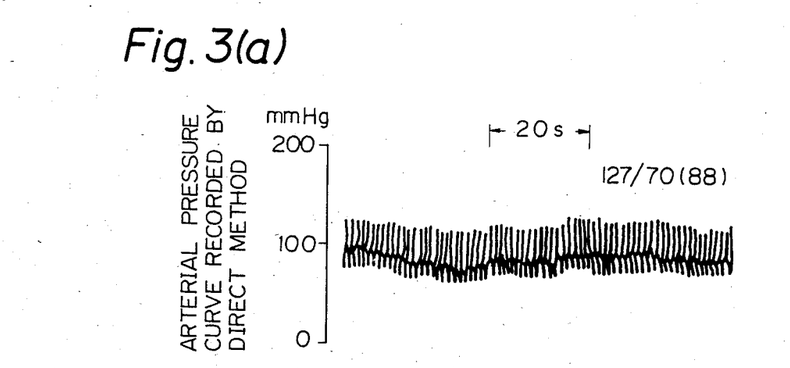
FIG. 3(a) is an arterial pressure curve recorded by the direct method.
Figure 3B:
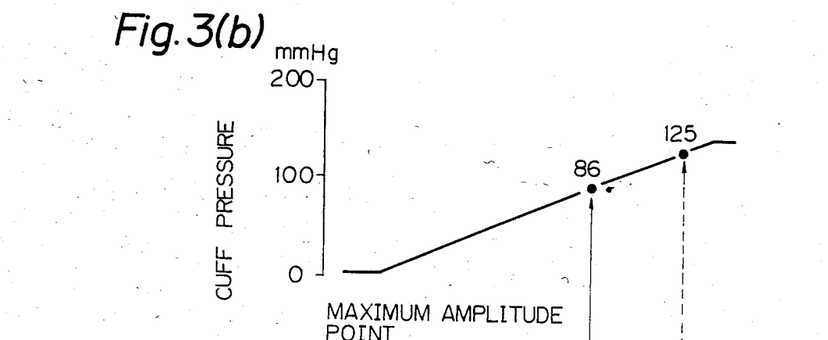
FIG. 3(b) is a diagram showing the interrelation between internal cuff pressure and pulse wave amplitude.
Figure 3C:
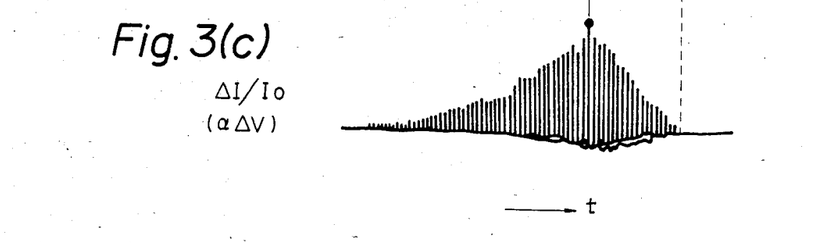
FIG. 3(c) is a pulse wave oscillation amplitude curve.
Figure 4A:
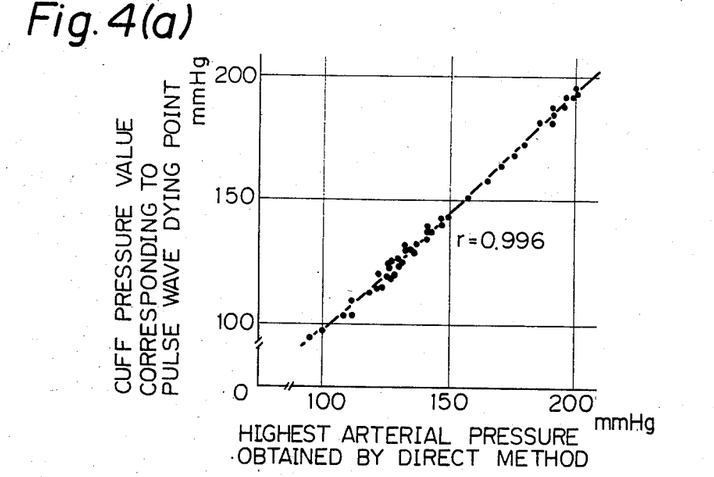
FIG. 4(a) is a diagram showing the relationship between systolic pressure measured by the direct method and systolic pressure measured by the indirect method.
Figure 4B:
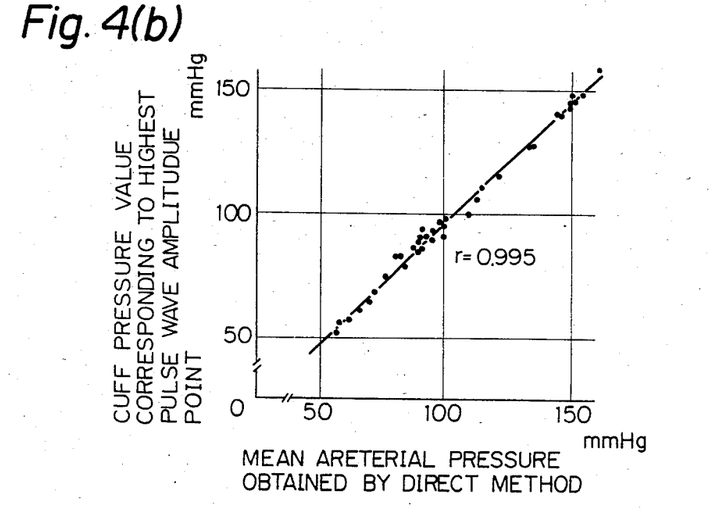
FIG. 4(b) is a diagram showing the relationship between mean arterial pressure measured by the direct method and mean arterial pressure measured by the indirect method according to the present invention.

Here, when the internal compression cuff pressure is increased gradually, the transmural pressure Pt (means arterial pressure) Pam-cuff compression pressure decreases. At this time, due to the non-rectilinearity of the blood vessel system pressure-volume relationship, the amplitude of ΔI/I increases or decreases as the cuff pressure Pc does. That is, as shown in FIG. 3, FIG. 3(a) is an arterial pressure curve recorded with respect to time by the direct method using the transducer 6, and systolic arterial pressure Pas=127 mmHg and mean arterial pressure Pam=88 Hg were detected, respectively whereas in FIGS. 3(b) (c) there are the cuff pressure Pc curve and the ΔI and I. comparison curve, respectively. Cuff pressure Pc corresponds to the maximum amplitude this ΔI/I. (ΔαV) point of pulse waves substantially coincides with mean arterial pressure Pam (86 mmHg) and cuff pressure Pc at pulse wave dying-out point coincides with systolic pressure Pas (125 mmHg). And as shown in FIGS. 4(a), (b), the relative coefficient of the systolic pressure recorded by the direct method and the systolic pressure based on the cuff pressure value corresponding to pulse wave dying point by the inventive indirect method is expressed by r=0.006 and similarly, the relative coefficient of mean arterial pressure by both the direct and indirect methods is expressed by:
r=0.0996

The details of these measurement methods have been reported by the following literature:
"Medical & Biological Engineering & Computing" 20, 307–313 (1982) and
"Medical & Biological Engineering & Computing" 20, 314–318 (1982)

Figure 5A:
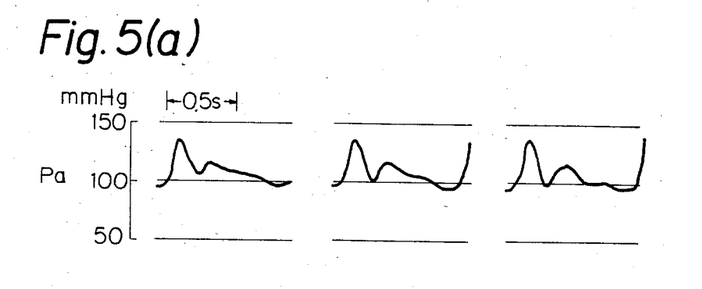
FIG. 5(a) is a diagram showing an internal blood vessel pressure Pa.
Figure 5B:
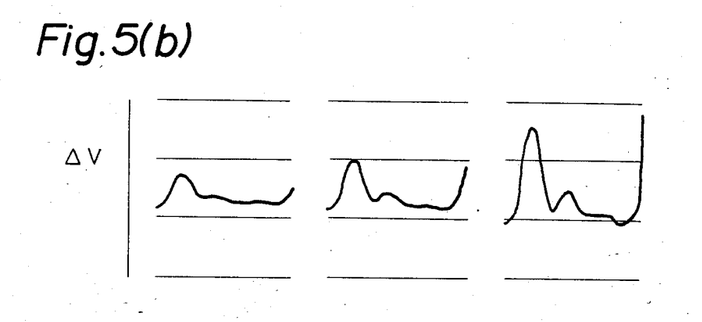
FIG. 5(b) is a diagram showing the volume variation wave form ΔV.
Figure 5C:
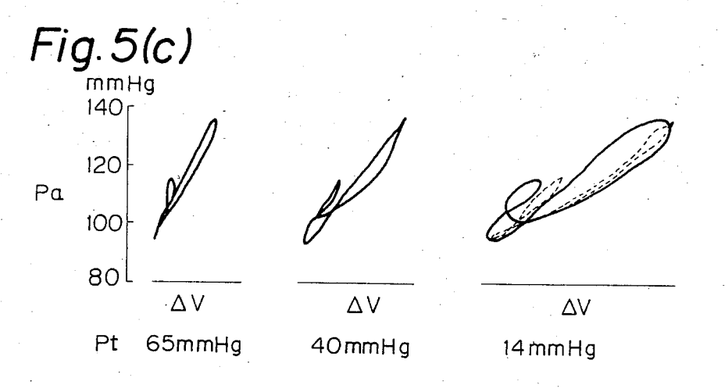
FIG. 5(c) is a diagram showing the rectilinearity of wave forms Pa and ΔV.

Generally, arterial blood vessels have viscous and non-rectilinearity properties and in these arterial blood vessels, blood vessel internal pressure (i.e., arterial pressure Pa wave forms and volume variation ΔV wave forms do not necessarily correspond with each other. However, as shown in FIG. 5(a) which is an internal blood vessel pressure diagram Pa, FIG. 5(b) which is a volume variation ΔV wave form diagram and FIG. 5(c) which is a Pa and ΔV rectilinearity diagram, the viscous behavior of blood vessel walls is small when the transmural pressure Pt is not relatively large and the pressure volume characteristic can be made approximate to rectilinearity within the originally pulse pressure range provided that the error on the order of ±15%. And even when Pt is small, the pressure loop of the pressure-volume characteristic can be made rectilinear [see the dotted line in FIG. 5(c)] in the same manner by which the lag of rising phase is adjusted. That is, when pulse pressure is not excessively high, it can be said that the pressure wave forms and volume wave forms are in their respective paired relationship within the error range referred to hereinabove.

Figure 6A:
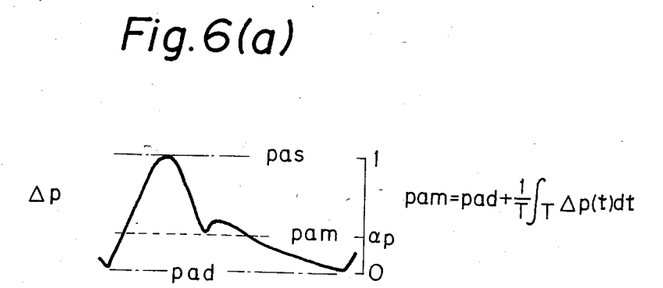
FIG. 6(a) is a diagram showing arterial pressure wave form Δp corresponding to one heart beat.
Figure 6B:
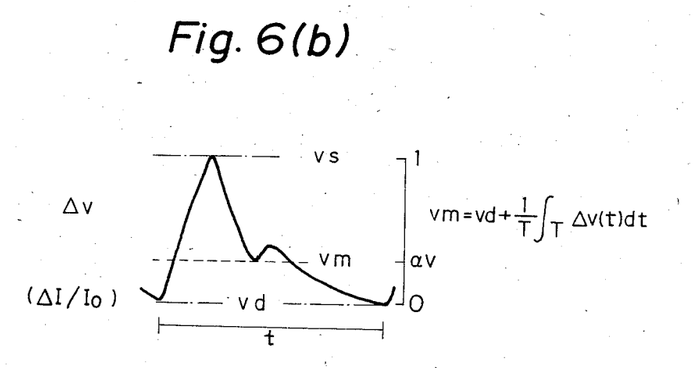
FIG. 6(b) is a diagram showing volume wave forms corresponding to one heart beat.

Based on this conception, arterial pressure wave forms and volume wave forms corresponding to one heart beat is shown in FIG. 6.

First, as to arterial pressure pulse wave, as shown in FIG. 6(a), assuming that in one heart beat, the maximum value is Pas, the minimum value is pad, and the mean value is Pam, varying pressure wave form is Δp(t) and arterial pressure wave constant is αp, then the mean value Pam can be expressed by:

$$Pam = Pad + \frac{1}{T} \int_t \Delta p(t) dt \quad (3)$$

$$= Pad + \alpha p(pas - pad) \quad (4)$$

Thus, from the equation (4), the arterial pressure wave form constant Δp will be calculated by:

$$\alpha p = (Pam - Pad)/(Pas - Pad) \quad (5)$$

On the other hand, as to the volume pulse wave form, as shown in FIG. 6(b), assuming that in one heart beat, the highest value is vs, the lowest value is vd, and the mean value is vm, the varying volume wave form Δv(t) and the volume wave form constant is αv, then, the mean value mm can be represented by:

$$vm = vd + \frac{1}{T} \int_t \Delta v(t) dt \quad (6)$$

$$= vd + \alpha v(vs - vd) \quad (7)$$

thus, from the above-mentioned equation (7), the volume wave form constant Δv is calculated by:

$$\alpha v = (vm - vd)/(vs - vd) \quad (8)$$

Figure 7A:
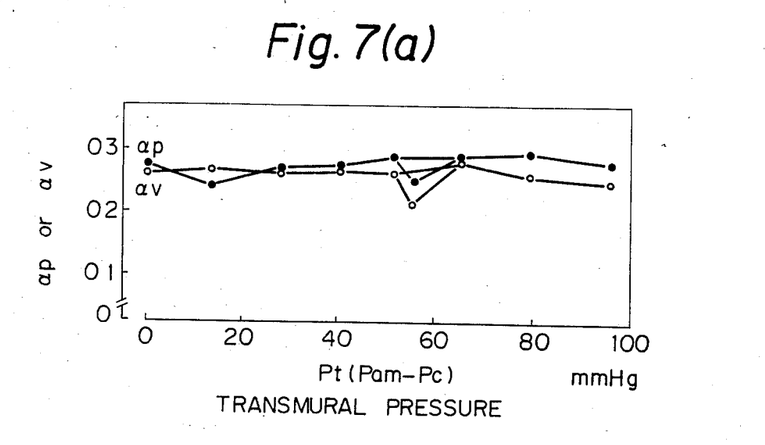
FIG. 7(a) is a diagram showing differences between arterial pressure wave form constants Δp and volume wave form constants Δv.

FIG. 7 shows the results by calculating αp, αv for various transmural pressures Pt (Pam−Pc) from internal blood vessel pressure wave forms directly measured using the blood vessel bed model as shown in FIG. 1 and the volume wave forms photoelectrically detected. That is, as shown in FIG. 7(a), even if the transmural pressure Pt varies, αp and αv are substantially constant and coincide with each other within the error range on the order of ±15%. Thus, it is apparent that αp and αv can be made as arterial pressure wave form constant and volume wave form constant, respectively.

When pressure wave form and volume wave form coincide with each other perfectly, αp and αv will have an equal value. At this time, highest arterial pressure value and mean arterial pressure are known by the above-mentioned methods, lowest arterial pressure value Pad can be obtained by employing αv indirectly defined in place of αp as follows:

$$Pad = Pam - (Pas - Pam)\frac{\alpha v}{1 - \alpha v} \quad (9)$$

And as to the arterial wave form constant Δp, by the utilization the fact that the arterial pressure pulse wave and variation in blood vessel diameter show a close resemblance, the minimum arterial pressure value can be simply sought by detecting the arterial wave form through measurement of displacement of the skin by the employment of the equation (9). Also in this case, when the highest arterial pressure value, and mean arterial pressure value are known, the minimum pressure value Pad can be obtained by employing αp:

$$Pad = Pam - (Pas - Pam)\frac{\alpha p}{1 - \alpha p} \quad (10)$$

Figure 7B:
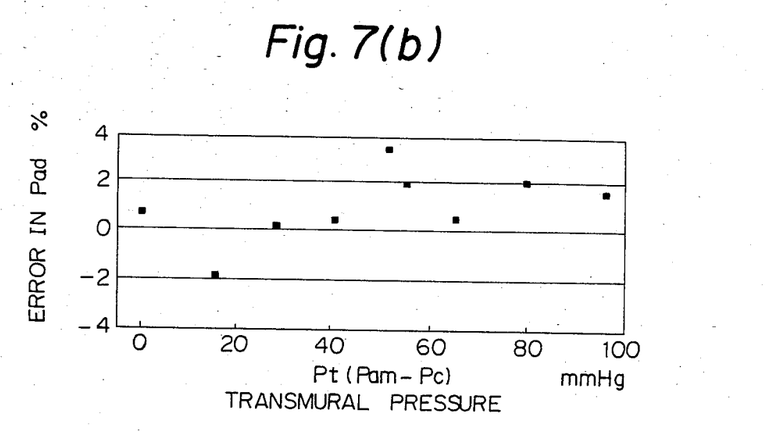
FIG. 7(b) is a diagram showing errors of diastolic arterial pressure values.

And as shown in FIG. 7(b), the lowest arterial pressure value obtained by the equations (9), (10) show an excellent accuracy within 2% error for the value actually measured by the direct measure.

As mentioned hereinabove, according to the present invention, a lowest arterial pressure value can be precisely sought from known highest, lowest arterial pressure and mean arterial values and arterial pressure wave forms, constant or volume wave form constant.

Next, the present invention will be described by way of embodiments thereof.

Figure 8:
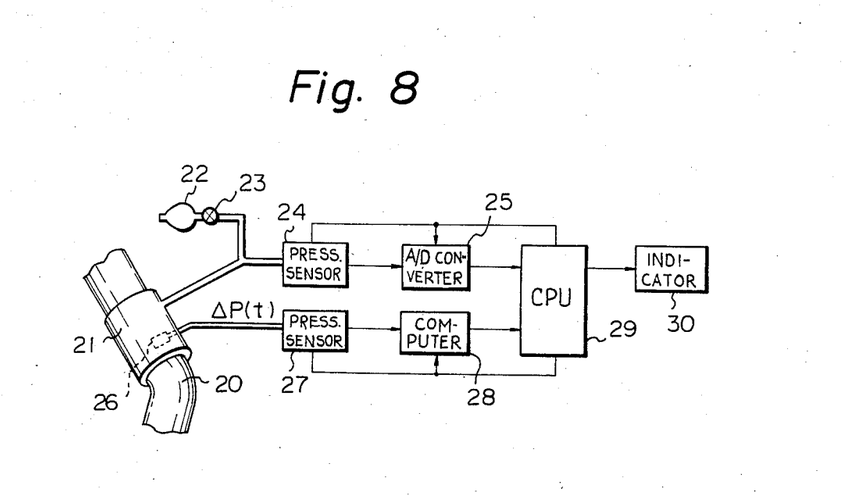
FIG. 8 is a schematic view of one embodiment of the arterial pressure measuring apparatus according to the present invention.

FIG. 8 shows one embodiment of arterial pressure measuring apparatus for detecting arterial pressure pulse wave in the upper arm of a human body. In this figure, 20 denotes the human upper arm, 21 denotes a cuff for pressurizing the upper arm, 22 denotes a pressure application rubber bulb, 23 denotes a cuff pressure reducing means, 24 denotes a pressure sensor for detecting the internal cuff pressure, 25 denotes an A/D converter, 26 denotes a rubber-made air bag of small volume interposed between the upper arm 20 and cuff 21, 27 denotes an arterial pressure pulse wave detection sensor (pressure sensor), 28 denotes a wave form constant computer, 29 denotes a microcomputer (which will be referred to as "CPU" for controlling sequence and for computing lowest arterial pressure valves and 30 denotes an indicator.

In carrying out the arterial pressure measurement by the use of the apparatus of FIG. 8, as shown in FIG. 8, first of all, the rubber bulb 22 inflates the cuff 21 to raise the internal pressure within the cuff 21 to a value above the systolic arterial pressure of the human whose arterial pressure is to be measured and thereafter, the internal cuff pressure is gradually reduced by the cuff pressure reducing means 23. When the internal cuff pressure is reduced to the systolic pressure value, an output signal begins to appear rapidly in the arterial through the air bag 26. By the sequence control provided by the CPU, the internal cuff pressure is measured by the systolic pressure value Pas at the output of the A/D converter 25 which is converting the output of the pressure sensor 24 from ANALOG to DIGITAL. Furthermore, as the internal cuff pressure drops, the amplitude of the output of the arterial pulse wave detection sensor 27 increases until a predetermined maximum amplitude is reached whereafter the amplitude begins to decrease. In the process, similarly, by the sequence control provided by the CPU 29, the storing and erasing of the output condition of A/D converter 25 each time the arterial pressure pulse wave detection sensor 27 produces an output (when the sensor 27 produces each output, if the amplitude value at the production of the output is larger than the amplitude of the output just prior to the first-mentioned output, the just-prior output value is erased and the output value following the same is stored and on the other hand, when the amplitude value of the following output is smaller than that of the just-prior output, the previously written output of the converter 25 is stored as it is) are repeated whereby the internal cuff pressure at the maximum amplitude of the arterial pulse wave as mean arterial pressure value Pam can be determined.

Figure 10:
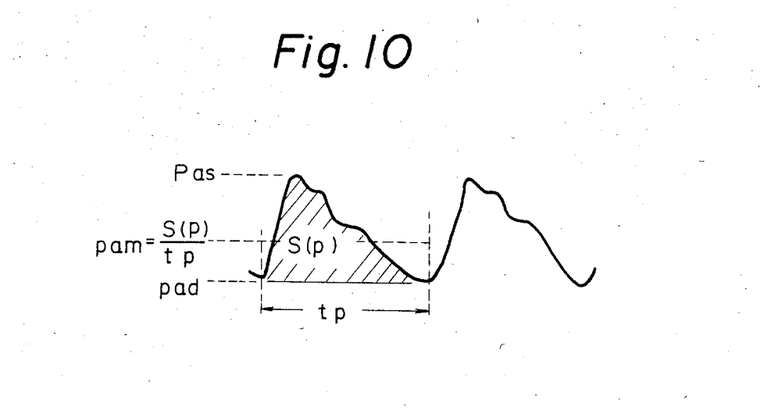
FIG. 10 is a diagram of one heart beat wave form of arterial pressure pulse wave on an enlarged scale.

And by the sequence control provided by the CPU 29, after a predetermined time after the mean arterial pressure has been measured, the measurement of arterial pressure wave form constant is intiated. When the output wave form of the arterial pressure pulse wave detection sensor corresponding to one heart beat is enlarged, the wave form is as shown in FIG. 10. The highest and lowest amplitude values from the zero or a predetermined level of this wave form are measured as highest value Pas and lowest value Pad, respectively, by peak value holding and reverse peak value holding detection operations and when the area value of one pulse wave is measured as S(p) and repeating time of pulse wave is measured as tp, the mean value of one pulse wave can be obtained from Pam=S(p)/tp by integrating operation. From the maximum value Pas, the minimum value Pad and the mean value Pam, the arterial wave form constant αp is obtained as αp=(Pam−Pad)/(Pas−Pad) by a wave form constant operation unit 28.

And in order to seek the arterial pressure wave form constant αp accurately, several pulse waves are sampled and the average of the values of these sampled pulse waves is sought.

From the sought maximum arterial pressure value Pas, mean arterial pressure value Pam and arterial wave form constant αp, the CPU 29 operates to seek the highest arterial pressure value Pad by:

$$Pad = Pam - (Pas - Pam)\frac{\alpha p}{1 - \alpha p}$$

These highest, mean and lowest arterial pressure values are indicated by the indicator 30.

And the CPU 29 may have the function of the wave form constant operation unit.

Figure 11:
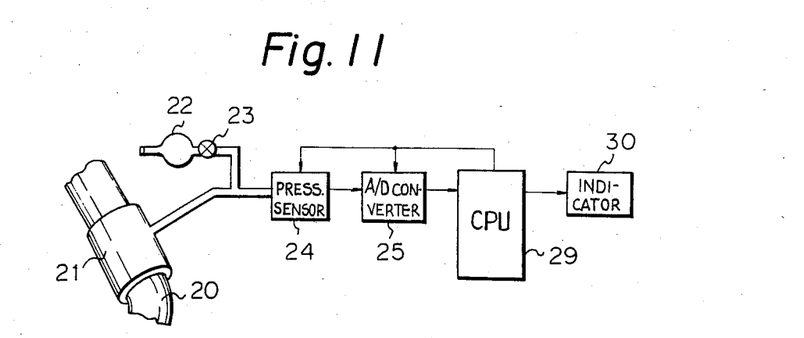
FIGS. 11 and 12 are schematic views of other embodiments of the arterial pressure measuring apparatus of the present invention.

Although the embodiment of FIG. 8 employs that air bag 26 in addition to the cuff 21 as arterial pressure pulse wave detection means, for simplification purpose, the cuff 21 itself may be utilized as detection means for seeking the arterial pressure pulse wave constant αp and such an embodiment is shown in FIG. 11. In this embodiment, as the A/D converter 25, the converter having a resolving power (a resolution power over 12 bits, for example) is employed and the lowest arterial pressure value Pad and arterial wave form constant αp in the manner as mentioned just above utilizing the operation function of the CPU 29. The measurement of the highest arterial pressure value Pas and the mean arterial pressure value Pam is conducted in the same manner as mentioned hereinabove.

And in order to further improve the reliability of the measurement, the lowest arterial pressure value can be also determined by the use of means such as a value obtained by operating the arterial wave form constant, highest arterial pressure value and mean arterial pressure value, a characteristic change of arterial pulse wave form, a dying-out point of a changing point adjacent to the lowest arterial pressure of arterial pulse waves provides a microphone's Korotkov sound, and a change point adjacent to the lowest arterial value in the differential value of arterial pulse waves.

Figure 12:
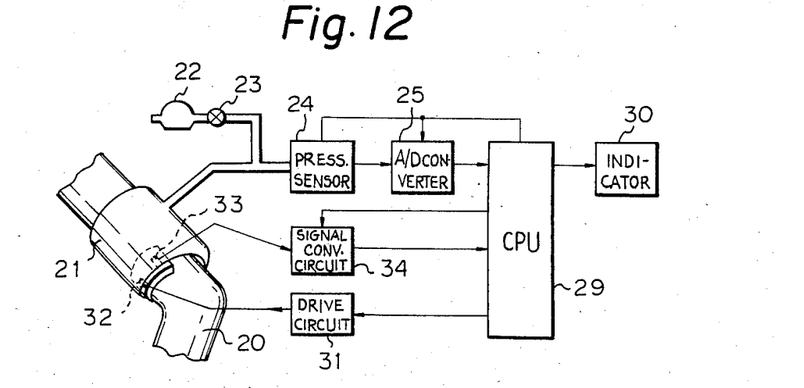

And FIG. 12 shows another embodiment of the present invention in which a lowest arterial pressure is detected by replacing arterial pressure wave form by volume pulse wave constant. This embodiment is adapted to detect volume pulse wave form as photoelectric volume pulse wave form. In FIG. 12, 31 denotes a light emitting element drive circuit, 32 denotes an infrared ray light emitting diode as a light receiving element, 33 denotes a phototransistor as a light receiving element, 34 denotes a light receiving and signal converting circuit. And the components having the same reference numerals as those in the previous embodiments will not be described.

In the detection of photoelectric volume pulse wave form, the light emitting element drive circuit 31 drives the infrared light receiving diode 32 which in turn emits infrared light to apply the light to the human upper arm whereupon the light is affected by the infrared ray absorption material such as hemoglobin within the upper arm arteria and the variation in light amount caused by the absorption of the light is detected by the phototransistor 33. As described hereinabove in connection with the principle of the invention, the invention utilizes the phenomenon that the amount of received light is in proportion to the amount of liquid within the upper arm blood vessel.

Figure 9:
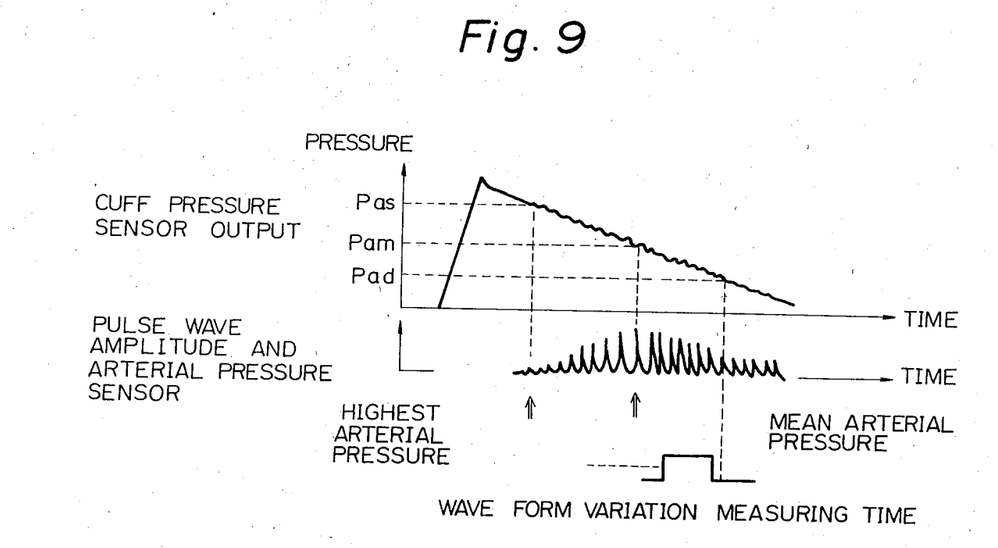
FIG. 9 is a diagram showing relations for measuring systolic and mean arterial pressures from variation in internal cuff pressure and generation of arterial pressure pulse waves.
Figure 13:
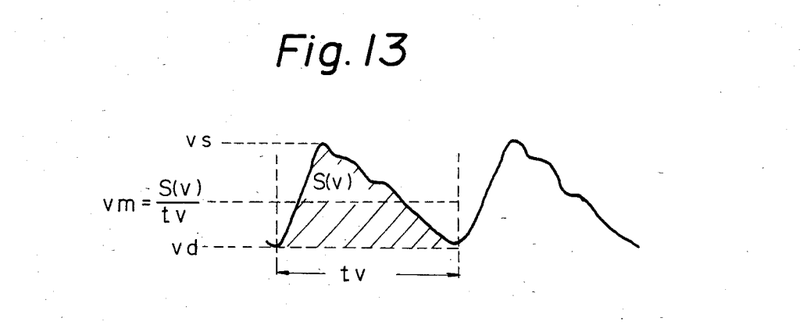
FIG. 13 is a diagram on an enlarged scale of one heart beat wave form of volume pulse wave.

By utilizing the volume pulse wave form detected at this time, arterial pressure values are sought in the manner similar to that described hereinabove referring to FIGS. 8 through 10. The highest arterial pressure value Pas and the mean arterial pressure value Pam are measured from volume pulse wave form and cuff pressure sensor output. And as shown in FIG. 13, highest amplitude values and lowest amplitude values are measured as highest values vs and lowest values vd, respectively from volume pulse wave forms corresponding to one heart beat. Furthermore, when one pulse wave area value is measured as S(v) and repeating time of pulse wave is measured as tv and furthermore, the mean value vm of one pulse wave is obtained by the equation:

$$vm = S(v)/tv.$$

From these highest, lowest and mean values vs, vd and vm, volume wave form constant $\alpha v$ is obtained $$\alpha v = \frac{vm - vd}{vs - vd}$$

Furthermore, as mentioned hereinabove, the accuracy of volume wave form constant can be enhanced by sampling several volume pulse waves.

From the thus sought highest arterial pressure value Pas, the mean arterial pressure value Pam and volume wave form constant $\alpha v$, the lowest arterial pressure value Pad is obtained by:

$$Pad = Pam - (Pas - Pam)\frac{\alpha v}{1 - \alpha v}$$

And these highest, mean and lowest arterial values are indicated by the indicator 30.

The measurement and operation of the above-mentioned various values can be simply performed by the CPU 29.

The above-mentioned highest value vs, lowest value vd, mean value vm, volume wave form constant $\alpha v$ or highest value Pas, the lowest value Pad, the mean value Pam and arterial pressure constant $\alpha p$ can be handled by multiplying proportional coefficients if necessary to compensate for differences between these values and actual measurement results.

Furthermore, the volume pulse wave detection system can seek similarly by employing the impedance-Plethysmo system and volume Plethysmo process employing liquid or gaseous body in addition to the photoelectric system of this embodiment.

Still furthermore, although the arterial pressure measurement area where the various embodiments are applied is the upper arm of a human body, the area where the present invention is applicable may be the upper and lower limbs and finger tip of a human body at which arterial pressure can be measured by cuff pressure application.

As mentioned hereinabove, the arterial pressure measuring apparatus of the present invention is adapted to set an arterial pressure wave form constant or volume wave form representing particular values in arterial pressure pulse waves and operate from the relationship between highest and mean arterial pressure values. As compared with actual measurement values by the direct method, the measurement values model blood vessel by the indirect method by the present invention are accurate and quite effective.

It will be apparent to those skilled in the art that various changes may be made in the invention without departing from the spirit and scope thereof.

What is claimed is:

1. A non-invasive arterial pressure measuring apparatus for detecting arterial pressure, comprising:
   systolic pressure value Pas measuring means including a cuff adapted to be applied to a limb of a body having arterial pressure for inflation of the cuff to raise the internal pressure therein to a value above the systolic arterial pressure of the body whose arterial pressure is to be measured by the systolic pressure value Pas and for gradually reducing the pressure to the systolic pressure;
   sequence control means coupled with said cuff for measuring the output thereof at a highest arterial pressure value Pas and responsive to said cuff output for storing the highest amplitude output while discarding previous lower amplitude outputs and non-storing of subsequent lower amplitude outputs to obtain and provide a mean arterial pressure value Pam; and
   means coupled with said cuff and responsive thereto for determining the lowest arterial pressure value Pad.

2. Apparatus as claimed in claim 1, wherein:
   said sequence control means includes an arterial pressure pulse wave detection sensor including a central processing unit and a pulse wave detection sensor; and
   said lowest arterial pressure value determining means includes a wave form constant operation unit having its inputs coupled to said arterial pressure pulse wave detection sensor and said central processing unit, and an output coupled to said central processing unit, said constant operation unit determining said minimum value Pad and being responsive to said pulse wave detection sensor thereby producing an arterial wave form constant $\alpha p$, wherein said arterial wave form constant $\alpha p$ is defined by the equation:

$$\alpha p = \frac{Pam - Pad}{Pas - Pad},$$

and the lowest arterial pressure value Pad is calculated by $$Pad = Pam - (Pas - Pam)\frac{\alpha v}{1 - \alpha v}.$$

3. Apparatus as claimed in claim 2, including a pressure sensor coupled to the cuff and an analog to digital converter having one of its inputs coupled to said pressure sensor and another of its inputs coupled, providing sequence control thereto, to said central processing unit thereby sequence controlling the output of said pressure sensor and converting the output thereof to digital and maintaining in said central processing unit the highest Pas applied from said analog to digital converter.

4. Apparatus as claimed in claim 3, wherein said central processing unit includes means responsive to the output of said arterial pressure pulse value detection sensor for sequence controlling the measurement of arterial pressure Pam, by peak value holding the highest value Pas and reverse peak value holding the lowest value Pad to measure the area value of one pulse wave as $S_{(p)}$ during a repeating time of $t_{(p)}$ to provide by integration the mean value of one pulse wave as follows:

$$Pam = S_{(p)}/t_{(p)},$$

said control processing unit feeding the output mean value Pam to said wave form constant operation unit.

5. Apparatus as claimed in claim 2, including:
photoelectric means coupled with said cuff for producing a volume pulse wave form output responsive to volume;
said central processing unit being coupled to said photoelectric means and to said cuff and being responsive to the highest arterial pressure value Pas and the mean arterial pressure value Pam as measured from the output of said cuff and said photoelectric means.

6. Apparatus as claimed in claim 5, wherein said photoelectric means includes a light receiving and signal converting circuit providing output to vs representative of the highest amplitude values and other outputs representative of the highest amplitude values vd, from volume pulse wave forms corresponding to one heart beat, the pulse wave area value being measured as $S_{(v)}$ for each repeating time to $t_{(v)}$, the mean value being as follows:

$$Vm = S_{(v)}/tv$$

and the volume wave form constant being defined as follows:

$$\alpha v = \frac{vm - vd}{vs - vd},$$

and the lowest arterial pressure value being defined as follows:

$$Pad = Pam - (Pas - Pam)\frac{\alpha v}{1 - \alpha v}.$$

7. Apparatus as claimed in claim 6, wherein said central processing unit includes multiplier means for multiplying at least one of the highest values vs, lowest values vd, mean values vm and volume wave form constant $\alpha v$ as multiplied by a proportional coefficient.

8. Apparatus as claimed in claim 5, wherein said photoelectric means includes:
a light emitting drive circuit having its input coupled to the output of said central processing unit;
a light receiving element in said cuff including an infrared light emitting diode which emits light responsive to said light emitting drive circuit; and
a phototransistor having a input coupled to said central processing unit and responsive to light emitted from said diode after it passes through the limb on which said cuff is positioned and responsive to variation in light caused by absorption and having its output coupled to said central processing unit, the output being in proportion to the amount of liquid within the blood vessel in the limb.

9. Apparatus as claimed in claim 1, wherein said cuff includes:
detection means for detecting the maximum arterial pressure Pas, the lowest arterial pressure Pad; and said central processing unit includes means to control pressure sensor means for sequence controlling the measurement of the arterial pressure to measure the mean arterial pressure Pam by peak value holding the highest value Pas and reverse peak holding the lowest value Pad to measure the area value of one pulse wave as $S_{(p)}$ during a repeating time of $t_{(p)}$ to provide by integration the mean value of one pulse wave as follows:

$$Pam = S_{(p)}/t_{(p)};$$

said central processing unit determining the arterial wave form constant $\alpha p$ which is defined by the equation $$\alpha p = \frac{Pam - Pad}{Pas - Pad},$$

and the lower arterial pressure value is defined as follows:

$$Pad = Pam - (Pas - Pam)\frac{\alpha p}{1 - \alpha p}.$$

10. A non-invasive method for measuring arterial pressure, comprising the steps of:
raising the internal pressure within a cuff applied to a human or other animal above the systolic arterial pressure thereof whose arterial pressure is to be measured;
obtaining more than one arterial pressure and selecting the highest arterial pressure value Pas in a central processing unit;
obtaining the output wave form of an arterial pressure pulse wave detection sensor corresponding to one heart beat and enlarging the waveform; and measuring the highest and lowest amplitude values from a predetermined reference level as highest value Pas and lowest value Pad.

11. The method of claim 10, wherein more than one arterial pressure is obtained by gradually reducing the internal cuff pressure to the systolic pressure value and then raising the pressure in the cuff and applying it to the central processing unit which will accept it and store it, if it is higher than a previously stored value to obtain the highest systolic pressure value Pas.

12. The method of claim 10, wherein the highest value Pas and lowest value Pad are measured respectively by peak value holding and reverse peak value holding detection operations; and the area value of one pulse wave form is $t_p$, the mean value of one pulse wave being obtained by an integrating operation:

$$Pam = S_{(p)}/t_p.$$

13. The method of claim 12, including sampling a number of pulse wave forms to obtain the arterial pressure wave form constant $\alpha p$, and said central processing unit seeking the highest arterial pressure value Pad by:

$$Pad = Pam - (Pas - Pam)\frac{\alpha p}{1 - \alpha p}.$$

14. The method of claim 13, wherein the arterial wave form constant is obtained by a wave form constant operation unit which is responsive to the central processing unit, where $$\alpha p = \frac{Pam - Pad}{Pas - Pad}.$$

15. The method of claim 12, including utilizing the cuff as a detection means for obtaining the arterial pressure pulse wave constant $\alpha p$, wherein the operational function of the central processing unit is used to obtain the lowest arterial pressure Pad, the arterial pressure constant $\alpha p$ being obtained by sampling a number of pulse wave forms to obtain the mean arterial pressure value Pam, where $$\alpha p = \frac{Pam - Pad}{Pas - Pad}$$

and the lowest arterial pressure value Pad is obtained as follows:

$$Pad = Pam - (Pas - Pam)\frac{\alpha p}{1 - \alpha p}.$$

16. The method of claim 10, wherein the lowest arterial pressure Pad is detected by a volume pulse wave form constant $\alpha v$ from which is obtained a highest value vs, a lowest value vd and a mean value vm in a volume pulse wave in a wave form corresponding to one heart beat from the equation:

$$v = \frac{vm - vd}{vs - vd},$$

wherein one pulse wave area value is measured as $S_{(v)}$ and the repetitive time of the pulse wave is measured as tv, and the mean value vm is obtained from the equation:

$$vm = S_{(v)}/t_v.$$

17. The method of claim 16, including:
detecting the volume pulse wave form as a photoelectric volume pulse wave form;
said detecting step including driving an infrared light receiving diode in the cuff to emit infrared light;
applying the infrared light to hemoglobin in the limb arteria for affecting light by absorption to vary the light;
detecting the cuff pressure sensor output by determining the variation in light amount, the amount of received light detected being in proportion to the amount of liquid with the limb blood vessel.

18. The method of claim 17, wherein:
the highest arterial pressure value Pas and the mean arterial pressure value Pam are measured from the volume pulse wave form and the cuff pressure sensor output;
the volume wave form constant $\alpha v$ has the following relationship to the highest value vs, the mean value vm, and the lowest values vd:

$$v = \frac{vm - vd}{vs - vd};$$

and the lowest arterial pressure value Pas is derived as follows:

$$Pad = Pam - (Pas - Pam)\frac{\alpha v}{1 - \alpha v}.$$

19. The method of claim 18, including the step of multiplying the highest value Vm, the lowest value vd, the mean value Vm, the volume wave form constant $\alpha v$, the highest value Pas, lowest value Pad and the mean value Pam by proportional coefficients to compensate for differences between these values and actual measured results.

20. Apparatus for measuring arterial pressure in human fingers, comprising:
a cuff for placement over the finger;
light emitting means within said cuff proximate to the finger, and
light receiving means within said cuff proximate to the finger;
first transducer means for measuring arterial pressure directly;
pump means for controlling said cuff and means for controlling said pump means;
second transducer means coupled to said cuff for measuring pressure therein;
current control circuit means for said light emitting means coupled thereto;
DC amplifier circuit means and AC amplifier circuit means coupled to the output of said light receiving means; and
operation circuit means coupled to the outputs of both said DC amplifier circuit means and said AC amplifier circuit means for producing an output characteristic of the ratio of the output of said AC amplifier circuit means to that of said DC amplifier circuit means, said ratio increasing and decreasing as the cuff pressure increases or decreases, respectively.

* * * * *